(12) United States Patent
Pham et al.

(10) Patent No.: US 9,434,662 B2
(45) Date of Patent: Sep. 6, 2016

(54) INTEGRATED FLUID CATALYTIC CRACKING AND ALKYLATION PROCESS

(71) Applicant: UOP LLC, Des Plaines, IL (US)

(72) Inventors: Trung Pham, Mount Prospect, IL (US); Susie C. Martins, Carol Stream, IL (US); Douglas A. Nafis, Mt. Prospect, IL (US)

(73) Assignee: UOP LLC, Des Plaines, IL (US)

( * ) Notice: Subject to any disclaimer, the term of this patent is extended or adjusted under 35 U.S.C. 154(b) by 400 days.

(21) Appl. No.: 14/229,437

(22) Filed: Mar. 28, 2014

(65) Prior Publication Data

US 2015/0274613 A1 Oct. 1, 2015

(51) Int. Cl.
*C07C 2/58* (2006.01)
*C07C 5/41* (2006.01)
*C07C 7/00* (2006.01)

(52) U.S. Cl.
CPC ............. *C07C 7/005* (2013.01); *C07C 2/58* (2013.01); *C07C 5/41* (2013.01)

(58) Field of Classification Search
None
See application file for complete search history.

(56) References Cited

U.S. PATENT DOCUMENTS

| | | | |
|---|---|---|---|
| 2,429,718 A | 10/1947 | Harding | |
| 2,816,150 A | 12/1957 | Hepp | |
| 3,658,693 A | 4/1972 | Hettick et al. | |
| 4,179,353 A * | 12/1979 | Hutson, Jr. ............ | C10G 35/00 208/135 |
| 4,426,276 A | 1/1984 | Dean et al. | |
| 5,196,574 A | 3/1993 | Kocal | |
| 5,254,743 A | 10/1993 | Holmgren et al. | |
| 6,177,601 B1 | 1/2001 | Bogdan et al. | |
| 6,315,964 B1 | 11/2001 | Knifton et al. | |
| 6,617,481 B1 | 9/2003 | Kulprathipanja et al. | |
| 6,632,971 B2 | 10/2003 | Brown et al. | |
| 6,653,518 B2 * | 11/2003 | Feng ..................... | C07C 5/41 585/418 |
| 7,439,409 B1 | 10/2008 | Jan et al. | |
| 7,728,185 B2 | 6/2010 | Senetar et al. | |
| 8,066,868 B1 * | 11/2011 | Zimmermann ........ | C10G 21/00 208/100 |
| 8,524,962 B2 | 9/2013 | Senetar et al. | |
| 2012/0071701 A1 | 3/2012 | Glover | |
| 2013/0296621 A1 | 11/2013 | Iaccino et al. | |

OTHER PUBLICATIONS

McDonald, G.W.G "Refinery economics affected by FCC impact on alkylation," Technology—Oil & Gas Journal (1985), 83(13), 111-115.
Anonymous, "New process produces alternative oxygenate from propylene," Oil & Gas Journal (1992), 90(21), 39-41.
Chaput et al. "Pretreat alkylation feed," Hydrocarbon Processing (1992), 71 (9), 51-54.
Dean et al. "Increasing FCC Propylene Yield," Saudi Aramco Journal of Technology (2005), Fall issue, 44-51.

* cited by examiner

*Primary Examiner* — In Suk Bullock
*Assistant Examiner* — Alyssa L Cepluch

(57) ABSTRACT

An integrated hydrocarbon conversion process is described. The process includes contacting a heavy hydrocarbon feedstock with a hydrocarbon cracking catalyst in a fluidized reactor zone to produce light olefins to form a fluid catalytic cracker (FCC) effluent stream comprising a range of hydrocarbons. The FCC effluent stream is separated to form at least a stream rich in $C_4$ hydrocarbons which comprises isobutane and 1-butene. The stream rich in $C_4$ hydrocarbons is introduced into an alkylation reaction zone where the isobutane and the 1-butene are alkylated to form a reaction product mixture comprising dimethylhexanes and $C_{9+}$ hydrocarbons. The reaction product mixture is dehydrocyclized to form a stream rich in xylenes.

16 Claims, 2 Drawing Sheets

INTEGRATED FLUID CATALYTIC CRACKING AND ALKYLATION PROCESS

BACKGROUND OF THE INVENTION

Fluid catalytic cracking (FCC) and alkylation technology are important processes for refineries to produce fuels and petrochemicals. Demand for propylene as well as aromatics is expected to continue to grow over the next decade.

Consequently, refineries need the flexibility to operate in either a fuel production mode or a petrochemical production mode by adjusting the operation severity of the processes. Refineries will switch to petrochemicals production when the price gap between propylene and xylenes and traditional fuels, such as gasoline, is high.

There is a need for flexible processes that can produce increased amounts of propylenes and xylenes while still being able to produce traditional fuels when needed.

SUMMARY OF THE INVENTION

One aspect of the invention is an integrated fluid catalytic cracking and alkylation process. In one embodiment, the process includes contacting a heavy hydrocarbon feedstock with a hydrocarbon cracking catalyst in a fluidized reactor zone at effective conditions to produce light olefins to form a fluid catalytic cracker effluent stream comprising a range of hydrocarbons. The fluid catalytic cracker effluent stream is separated in a separation zone to form at least a stream rich in $C_4$ hydrocarbons, the stream rich in $C_4$ hydrocarbons comprising isobutane and 1-butene. The stream rich in $C_4$ hydrocarbons is introduced into an alkylation reaction zone. The isobutane and the 1-butene are alkylated in the alkylation reaction zone in the presence of an alkylation catalyst under alkylation conditions to form a reaction product mixture comprising dimethylhexanes and $C_{9+}$ hydrocarbons. The reaction product mixture is dehydrocyclized in an aromatization zone in the presence of a dehydrocyclization catalyst under dehydrocyclization conditions to form a stream rich in xylenes.

DETAILED DESCRIPTION OF THE INVENTION

Figure 1:
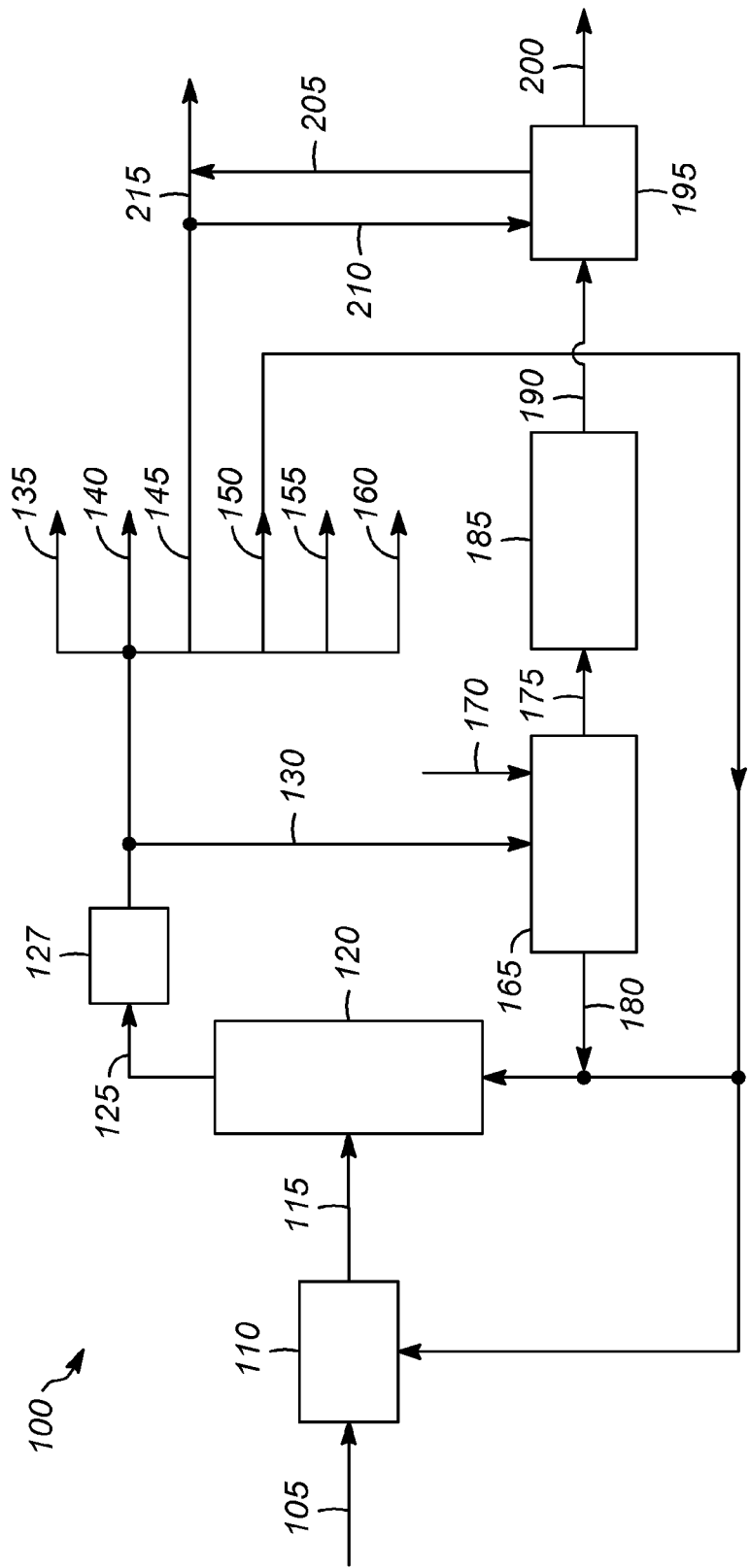
FIG. 1 is an illustration of one embodiment of a process for propylene and aromatics production using FCC and alkylation zones.

The present invention meets this need by providing an integrated FCC and alkylation process. The alkylation process makes an alkylate that is selective for dimethylhexane, making it suitable for xylene production. This alkylation process can be combined with FCC technology for petrochemical production. Products other than $C_8$ can be sent to the FCC reaction zone for cracking to propylene. The products from the conversion process include high yields of propylene (e.g., about 18-21 wt %), and high yields of alkylate that can be converted directly to xylenes.

The alkylation process produces 2,5-dimethylhexane which can be converted to p-xylene by dehydrocyclization. The alkylation also produces 2,3-dimethylhexane which can be converted to ortho-xylene and 2,4-dimethylhexane which can be converted to meta-xylene. Yields as high as 78% of $C_8$ hydrocarbons can be produced in the alkylation process.

By combining the alkylation process with the FCC process, the remaining alkylation products can be recycled back to the FCC zone for cracking to lighter products, including hydrocarbons.

The heavy products, including conjunct polymer from an ionic liquid regeneration process as discussed below, can be sent to the FCC zone using light cycle oil as a solvent. The light cycle oil can be a product of the FCC reactor.

Optionally, the light cycle oil stream can be routed to a hydrotreating zone and mixed with the feed stream to enrich its hydrogen content for additional naphtha and propylene production before being sent to the FCC reactor for processing.

The integrated process allows the use of both paraffins and olefins.

The alkylation product can be sent to an aromatization zone for dehydrocyclization. Trimethylpentane will not aromatize due to the lack of a 6 carbon chain length. Consequently, the majority of the high value alkylate will go through the aromatization zone without change at a temperature below 485° C. The high octane paraffins can be separated from the $C_{8+}$ aromatics by distillation. Toluene may be present in the alkylate cut because its boiling point overlaps with various alkylate components.

In some embodiments, the reaction product mixture from the alkylation process comprises predominantly dimethylhexanes and $C_{9+}$ hydrocarbons. It can be separated in to stream rich in dimethylhexanes and a stream rich in $C_{9+}$ hydrocarbons before dehydrocyclizing the reaction product mixture. The stream rich in dimethylhexanes can include $C_{7-}$ hydrocarbons, or the $C_{7-}$ hydrocarbons can be separated into at least one additional stream in the separation zone.

In other embodiments, all of the reaction product mixture is dehydrocyclized. In some embodiments, the dehydrocyclized reaction product mixture can then be separated into various components as desired.

Various types of alkylation catalysts can be employed, including HF, $H_2SO_4$, and ionic liquids. The HF alkylation process may produce a similar alkylate product to that of ionic liquids. The $H_2SO_4$ alkylate may be different because in the $H_2SO_4$ alkylation the butenes are converted to an equilibrium mixture of 1-butene and 2-butene before alkylation resulting in less 1-butene for reaction.

FIG. 1 illustrates one embodiment of an integrated alkylation and FCC process 100. A heavy hydrocarbon feed 105, such as vacuum gas oil (VGO) or atmospheric residue (AR), is sent to a hydrotreating zone 110 for hydrotreating. VGO has a true boiling point (TBP) cut point of 343° C. (650° F.) to 566° C. (1050° F.). AR has a TBP cut point of 343° C. (650° F.) to 1010° C. (1850° F.). The hydrotreating zone 110 can be a VGO hydrotreater for a VGO feed, or a Reduced Crude Desulfurization (RCD) unit if an AR feed is used.

Hydrotreating involves contacting hydrogen gas with the hydrocarbon stream in the presence of suitable catalysts which are primarily active for the removal of heteroatoms, such as sulfur, nitrogen, oxygen, and metals from the hydrocarbon feedstock. In hydrotreating, hydrocarbons with double and triple bonds may be saturated. Aromatics may also be saturated. Typical hydrotreating reaction conditions include a temperature of about 290° C. (550° F.) to about 455° C. (850° F.), a pressure of about 3.4 MPa (500 psig) to about 27.6 MPa (4000 psig), a liquid hourly space velocity of about 0.5 $hr^{-1}$ to about 4 $hr^{-1}$, and a hydrogen rate of about 168 to about 1,011 $Nm^3/m^3$ oil (1,000-6,000 scf/bbl). Typical hydrotreating catalysts include at least one Group VIII metal, preferably iron, cobalt and nickel, and at least one Group VI metal, preferably molybdenum and tungsten, on a high surface area support material, preferably alumina. Other typical hydrotreating catalysts include zeolitic catalysts, as well as noble metal catalysts where the noble metal is selected from palladium and platinum.

The hydrotreated heavy hydrocarbon feedstock 115 is sent to a FCC zone 120 (resid FCC (RFCC) zone is used for a resid feed). The feedstock 115 is cracked into lighter components in the FCC zone 120.

Fluid catalytic cracking (FCC) is a catalytic hydrocarbon conversion process accomplished by contacting heavier hydrocarbons in a fluidized reaction zone with a catalytic particulate material. The reaction in catalytic cracking is carried out in the absence of substantial added hydrogen or the consumption of hydrogen. The process typically employs a powdered catalyst having the particles suspended in a rising flow of feed hydrocarbons to form a fluidized bed. In representative processes, cracking takes place in a riser, which is a vertical or upward sloped pipe. Typically, a pre-heated feed is sprayed into the base of the riser via feed nozzles where it contacts hot fluidized catalyst and is vaporized on contact with the catalyst, and the cracking occurs converting the high molecular weight oil into lighter components including liquefied petroleum gas (LPG), gasoline, and a distillate. The catalyst-feed mixture flows upward through the riser for a short period (a few seconds), and then the mixture is separated in cyclones. The hydrocarbons are directed to a fractionator for separation into LPG, gasoline, diesel, kerosene, jet fuel, and other possible fractions. While going through the riser, the cracking catalyst is deactivated because the process is accompanied by formation of coke which deposits on the catalyst particles. Contaminated catalyst is separated from the cracked hydrocarbon vapors and is further treated with steam to remove hydrocarbon remaining in the pores of the catalyst. The catalyst is then directed into a regenerator where the coke is burned off the surface of the catalyst particles, thus restoring the catalyst's activity and providing the necessary heat for the next reaction cycle. The process of cracking is endothermic. The regenerated catalyst is then used in the new cycle. Typical FCC conditions include a temperature of about 400° C. to about 800° C., a pressure of about 0 to about 688 kPa g (about 0 to 100 psig), and contact times of about 0.1 seconds to about 1 hour. The conditions are determined based on the hydrocarbon feedstock being cracked, and the cracked products desired. Zeolite-based catalysts are commonly used in FCC reactors, as are composite catalysts which contain zeolites, silica-aluminas, alumina, and other binders.

The FCC effluent 125 is separated in separation zone 127 into several fractions. It can be separated into one or more of a $C_4$-rich stream 130, a gas fraction 135, a propylene-rich fraction 140, a gasoline fraction 145, a light cycle oil fraction 150, a Clarified Slurry Oil (CSO) fraction 155, and a coke fraction 160. The separation can take place by distillation, gas concentration (with stripper-absorber system and compression), fractionation, and cold box recovery (with compression and fractionation).

The $C_4$-rich stream 130 is sent to an alkylation zone 165. The $C_4$-rich stream comprises isobutane and/or 1-butene. It can also include n-butane, 2-butene and/or isobutene. Desirably, there is less than 50% total of 2-butene and isobutene in the alkylation zone %, or less than about 40 wt %, or less than about 30 wt %, or less than about 20 wt %, or less than about 10 wt %, or less than about 5 wt %, or less than about 1 wt %.

In some embodiments, an isobutane stream 170 can be introduced into the alkylation zone 165. In some embodiments, the isobutane stream 170 can be formed by isomerizing a stream comprising n-butane. In some embodiments, the n-butane stream can be an external stream. In other embodiments, the $C_4$-rich stream can be 130 isomerized before being introduced into the alkylation zone 165 to convert some of the n-butane into isobutane.

The isobutane and 1-butene are selectively converted to dimethylhexanes in the alkylation zone 165. The isobutane is added in excess, and only a portion of the isobutane reacts with the 1-butene, e.g., about 5 to about 20 wt %. The molar ratio of isobutane to olefin is typically in the range of about 5:1 to about 20:1, or about 8:1 to about 16:1.

The alkylation reaction also produces $C_{9+}$ hydrocarbons and $C_{7-}$ hydrocarbons.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. toluene, xylenes, ethylbenzene, etc.). For isobutene alkylation, typically, the reactants are mixed in the presence of a strong acid catalyst, such as sulfuric acid or hydrofluoric acid. The alkylation reaction is carried out at mild temperatures, and is typically a two-phase reaction. Because the reaction is exothermic, cooling is needed. Depending on the catalyst used, normal refinery cooling water provides sufficient cooling. Alternatively, a chilled cooling medium can be provided to cool the reaction. The catalyst protonates the alkenes to produce reactive carbocations which alkylate the isobutane reactant, thus forming branched chain paraffins from isobutane. Aromatic alkylation is generally now conducted with solid acid catalysts including zeolites or amorphous silica-aluminas.

The alkylation reaction zone is maintained at a pressure sufficient to maintain the reactants in liquid phase. For a hydrofluoric acid catalyst, a general range of operating pressures is from about 200 to about 7100 kPa absolute. The temperature range covered by this set of conditions is from about −20° C. to about 200° C. For at least alkylation of aromatic compounds, the volumetric ratio of hydrofluoric acid to the total amount of hydrocarbons entering the reactor should be maintained within the broad range of from about 0.2:1 to about 10:1, preferably from about 0.5:1 to about 2:1

Any suitable alkylation catalyst may be used. Typically, the catalysts are acidic. Suitable alkylation catalysts include, but are not limited to, hydrofluoric acid, sulfuric acid, and acidic ionic liquids. Other catalysts include zeolites having a zeolite framework type selected from the groups consisting of beta, MOR, MWW, FAU, and NES. Suitable zeolites include mordenite, ZSM-4, ZSM-12, ZSM-20, offretite, gmelinite, beta, NU-87, UZM-8, MCM-22, MCM-36, MCM-49, zeolite Y, zeolite X, and gottardite. Another class of acidic, solid catalysts are acidified refractory oxides such as chlorided, fluorided, or sulfated alumina, gallia, boria, molybdia, ytterbia, titania, chromia, silica, zirconia, and the like and combinations thereof. Clays and amorphous catalysts may also find utility. Further discussion of alkylation catalysts can be found in U.S. Pat. Nos. 5,196,574; 6,315,964B1 and 6,617,481B1. Newer alkylation catalysts can also be used in this process. For example, one such catalyst comprises a mixture of two types of zeolitic materials, where the zeolites are mixed and produced to have two zeolites within a single catalyst pellet, e.g., UZM-8 and a rare earth substituted X zeolite, Y zeolite, or a zeolite having an EMT/FAU intergrowth. When ionic liquid catalysts are used for the alkylation, typical alkylation reaction conditions include a temperature in the range of about −20° C. to about 100° C., or about −20° C. to about 70° C., or about 0° C. to about 70° C., or about 20° C. to about 70° C., or about 0° C. to about 60° C., or about 0° C. to about 50° C., or about 20° C. to about 60° C., or about 20° C. to about 50° C. It is preferred to have an ionic liquid that maintains its liquid state through the operating temperature range.

The pressure is typically in the range of atmospheric (0.101 MPa) to about 8.0 MPa, or about 0.300 MPa to about 2.5 MPa. The pressure is preferably sufficient to keep the reactants in the liquid phase.

The residence time of the reactants in the reaction zone is in the range of a few seconds to hours, or about 0.5 min to about 60 min, or about 5 min to about 60 min.

The molar ratio between isobutane and 1-butene is in the range of about 1:1 to about 50:1, or about 2:1 to about 50:1, or about 5:1 to about 30:1, or about 5:1 to about 25:1, or about 5:1 to about 20:1, or about 5:1 to about 15:1.

The catalyst is measured with respect to the amount of olefins, with a catalyst to olefin weight ratio between about 0.1:1 and about 10:1, or about 0.2:1 and about 5:1, or about 0.5:1 and 2:1.

Vigorous stirring is desirable to ensure good contact between the reactants and the catalyst.

In one embodiment, the ionic liquid and the isobutane are placed in the alkylation zone, and the 1-butene is added slowly at the reaction conditions. This provides low instantaneous olefin concentration, e.g., much greater than 100/1 isobutane/1-butene. It also provides shorter olefin residence time in the reactor, which favors the formation of dimethylhexane (DMH) over trimethylpentane (TMP). In one embodiment with a continuous reactor, the stream containing 1-butene can be added at multiple injection locations to reduce the local concentration of olefin.

The alkylation reaction has high conversion of 1-butene, typically at least about 70%, or at least about 80%, or at least about 90%, or at least about 95%, or at least about 97%, or at least about 99%.

The ionic liquid comprises an organic cation and an anion. Suitable cations include, but are not limited to, nitrogen-containing cations and phosphorus-containing cations. Suitable organic cations include, but are not limited to:

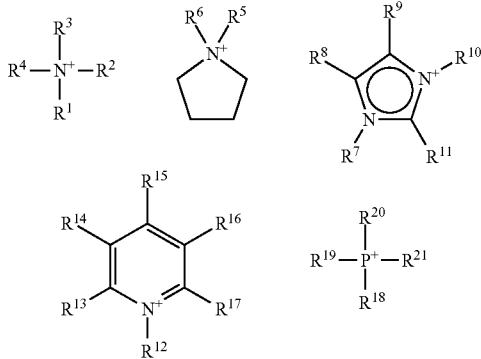

where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable.

The anion can be derived from halides, sulfates, bisulfates, nitrates, sulfonates, fluoroalkanesulfonates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the atom fraction of aluminum ranging from 0<Al<0.30 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

In some embodiments, the ionic liquid catalyst is a phosphonium based ionic liquid. In some embodiments, the anion of the ionic liquid is a haloaluminate, such as a chloroaluminate, or a bromoaluminate, or combinations thereof.

In some embodiments, the ionic liquid catalyst is combined with a Brønsted acid additive selected from the group consisting of HCl, HBr, HI and mixtures thereof, or acid precursors, such as sec-butylchloride or tert-butylchloride that break down to form a hydrogen halide acid.

Due to the low solubility of hydrocarbons in ionic liquids, olefins-isoparaffins alkylation, like most reactions in ionic liquids, is generally biphasic and takes place at the interface in the liquid phase. The catalytic alkylation reaction is generally carried out in a liquid hydrocarbon phase, in a batch system, a semi-batch system or a continuous system using one reaction stage as is usual for aliphatic alkylation.

The heat generated by the reaction can be eliminated using any of the means known to the skilled person. At the reactor outlet, the hydrocarbon phase is separated from the ionic liquid phase by gravity settling based on density differences, or by other separation techniques known to those skilled in the art.

The alkylation product typically contains at least about 50 wt % $C_8$ compounds, or at least about 60 wt %, or at least about 70 wt %, or at least about 75 wt %. The $C_8$ fraction contains various isomers of DMH and TMP. The ratio of DMH:TMP is typically at least about 2:1, or at least about 3:1, or at least about 4:1, or at least about about 5:1, or at least about 6:1, or at least about 7:1, or at least about 8:1, or at least about 9:1, or at least about 10:1, or at least about 15:1.

The alkylation product of 1-butene and isobutane is rich in DMH, including 2,3-DMH 2,4-DMH, and 2,5-DMH. The alkylation product typically contains at least about 30 wt % DMH, at least about 40 wt % DMH, or at least about 50 wt % DMH, or at least about 60 wt % DMH. Of the total DMH, typically at least about 25 wt % is 2,5-DMH, or at least about 30 wt %, or at least about 35 wt %, or at least about 40 wt %. Of the total DMH, typically at least about 25 wt % is 2,4-DMH, or at least about 30 wt %, or at least about 35 wt %, or at least about 40 wt %.

As shown, the alkylation reaction product is separated into a stream rich in dimethylhexanes 175 and a $C_{9+}$ hydrocarbon stream 180. The stream rich in dimethylhexanes 175 is sent to an aromatization zone 185 where the dimethylhexanes are dehydrocyclized to xylenes. Alternatively, all of the alkylation reaction product can be sent to the aromatization zone for dehydrocyclization (not shown).

Dehydrocyclization of the DMH rich stream or the alkylation reaction product stream can be performed at relatively low operating pressures. Operating conditions in a dehydrocyclization zone include a pressure of from about 100 kPa to 1.0 MPa (absolute), or about 100 to 500 kPa, or below about 300 kPa. Free hydrogen optionally is supplied to the process in an amount sufficient to correspond to a ratio of from about 0.1 to 10 moles of hydrogen per mole of hydrocarbon feedstock. By "free hydrogen" is meant molecular $H_2$, not combined in hydrocarbons or other compounds. Preferably, the reaction is carried out in the absence of added halogen. The volume of catalyst corresponds to a liquid hourly space velocity of from about 0.5 to 40 $hr^{-1}$. The operating temperature generally is in the range of about 260° C. to about 600° C.

The dehydrocyclization process produces an aromatics-rich effluent stream, with the aromatics content of the $C_{5+}$ portion of the effluent typically within the range of about 45 to 95 mass-%, and more usually more than about 85 mass-%. The composition of the aromatics depends principally on the feedstock composition and operating conditions, and comprises principally $C_6$-$C_{12}$ aromatics. $C_8$ aromatics are the principal aromatics produced from the DMH rich stream.

Paraffins and olefins in the DMH rich stream are converted selectively in the aromatization zone to the corresponding aromatics, i.e., most of the aromatics produced have the same number of carbon atoms as the paraffins or olefins from which they were converted. For example, DMH yields principally xylenes.

The dehydrocyclization catalyst can be any suitable dehydrocyclization catalyst.

Examples of suitable dehydrocyclization catalysts include Pt or Cr on alkali-modified alumina or other non-acidic supports. When Pt is used, modifiers such as Sn, In, Re, Ga, Ce, or La may be used to reduce undesired side-reactions, such as cracking, in favor of dehydrocyclization. These catalysts are described, for example, in U.S. Pat. No. 7,439,409, and Dehydrocyclization of Paraffins, J. of Catalysis, 23, 340-354 (1971), which are incorporated herein by reference. An essential ingredient of this type of dehydrocyclization catalyst is a metal component comprising at least one metal selected from Groups VIII (IUPAC 8-10) and IA of the Periodic Table, including the platinum-group metals, Fe, Co, Ni, Cu, Ag, and Au. Of the preferred Group VIII platinum-group metals, i.e., platinum, palladium, rhodium, ruthenium, osmium, and iridium, platinum is particularly preferred. Mixtures of platinum-group metals as a uniformly distributed component or platinum-group surface metals also are within the scope of this invention. The platinum-group metal component may exist within the final catalytic composite as a compound such as an oxide, sulfide, halide, or oxyhalide, in chemical combination with one or more of the other ingredients of the composite, or as an elemental metal. Best results are obtained when substantially all of the metals are present in the elemental state. The platinum-group metal component may be present in the final catalyst composite in any amount which is catalytically effective, but relatively small amounts are preferred. The uniformly distributed platinum-group metals generally will comprise from about 0.01 to 5 wt.-% of the final catalyst, and preferably about 0.05 to 2 wt.-%, calculated on an elemental basis.

The dehydrocyclization catalyst may contain a halogen component. The halogen component may be fluorine, chlorine, bromine, or iodine or mixtures thereof with chlorine being preferred. Considering the nonacidic nature of the support, the halogen usually is incorporated into the catalyst only in association with the incorporation of a metal component. The halogen component is generally present in a combined state with the inorganic-oxide support. The halogen component is preferably well distributed throughout the catalyst and may comprise from more than 0.2 to about 15 wt.-% calculated on an elemental basis, of the final catalyst.

The dehydrocyclization catalyst may contain supplemental metal components known to modify the effect of the preferred platinum component. Such metal modifiers may include one or more of the Group IVB (IUPAC 14) metals, Group 1b (IUPAC 11) metals, rhenium, indium, gallium, bismuth, zinc, uranium, thallium, and the rare earth (lanthanide) metals. Group VIa (IUPAC 6) metals are disfavored, considering the known toxicity of chromium. One or more of tin, indium, germanium, gallium, copper, silver, gold, lead, zinc, and the rare-earth elements are favored modifier metals, with tin, indium, germanium, cerium, and lead being particularly favored. If present, the concentration of a metal modifier in the catalyst may be within the range of 0.001 to 5.0 wt.-%. Catalytically effective amounts of such metal modifiers may be incorporated into the catalyst by any means known in the art. The ratio of tin to platinum in the finished catalyst affects catalyst performance, particularly conversion of paraffinic hydrocarbons at a given set of operating conditions. The Sn/Pt mass ratio preferably is above about 1.5, and more preferably at least about 2; in some cases, a ratio of 3 or more is advantageous.

It is essential that the dehydrocyclization catalyst be non-acidic, as acidity lowers the selectivity to para-xylene of the finished catalyst. The required nonacidity may be effected by any suitable method, including impregnation, co-impregnation with a platinum-group metal, or ion exchange.

The catalyst preferably comprises porous, adsorptive, high-surface-area materials. Within the scope of the present invention are refractory supports containing one or more of: (1) refractory inorganic oxides such as alumina, silica, titania, magnesia, zirconia, chromia, thoria, boria, or mixtures thereof, (2) synthetically prepared or naturally occurring clays and silicates, which may be acid-treated; (3) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations; (4) spinels such as $MgAl_2O_4$, $FeAl_2O_4$, $ZnAl_2O_4$; and (5) combinations of materials from one or more of these groups. The preferred refractory inorganic oxide will have an apparent bulk density of about 0.3 to about 1.1 g/cc and surface area characteristics such that the average pore diameter is about 20 to 1000 angstroms, the pore volume is about 0.05 to about 1 cc/g, and the surface area is about 50 to about 500 $m^2/g$.

An alternative suitable support having inherent nonacidity may be termed a "synthetic hydrotalcite" characterized as a layered double hydroxide or metal-oxide solid solution. Hydrotalcite is a clay with the ideal unit cell formula of $Mg_6Al_2(OH)_{16}(CO_3)\cdot 4H_2O$, and closely related analogs with variable magnesium/aluminum ratios may be readily prepared. These embodiments are solid solutions of a divalent metal oxide and a trivalent metal oxide having the general formula $(M^{+2}{}_xO)(M^{+3}{}_yO)OH_y$ derived by calcination of synthetic hydrotalcite-like materials whose general formula may be expressed as $(M^{+2})_x(M^{+3})_y(OH)_zA_q\cdot rH_2O$. $M^{+2}$ is divalent metal or combination of divalent metals selected from the group consisting of magnesium, calcium, barium, nickel, cobalt, iron, copper, and zinc. $M^{+3}$ is a trivalent metal or combination of trivalent metals selected from the group consisting of aluminum, gallium, chromium, iron, and lanthanum. Both $M^{+2}$ and $M^{+3}$ may be mixtures of metals belonging to the respective class: for example, $M^{+2}$ may be pure nickel or may be both nickel and magnesium, or even nickel-magnesium-cobalt; $M^{+3}$ may be solely aluminum or a mixture of aluminum and chromium, or even a mixture of three trivalent metals such as aluminum, chromium, and gallium. $A_q$ is an anion, most usually carbonate although other anions may be employed equivalently, especially anions such as nitrate, sulfate, chloride, bromide, hydroxides, and chromate. The ratio x/y of the divalent and trivalent metals can vary between about 2 and about 20, with the ratios of 2 to about 10 being preferred. The case where $M^{+2}$ is magnesium, $M^{+3}$ is aluminum, and A is carbonate corresponds to the hydrotalcite series. Calcination of such layered double hydroxides results in destruction of the layered structure and formation of materials which are effectively described as solid solutions of the resulting metal oxides. It is preferable that the $(M^{+2}_xO)(M^{+3}_yO)OH_y$ solid solution has a surface area at least about 150 $m^2/g$, more preferably at least 200 $m^2/g$ and it is even more preferable that it be in the range from 300 to 350 $m^2/g$. Preparation of Suitable Basic Metal-Oxide Supports is Described in Detail in U.S. Pat. No. 5,254,743.

Another example of a dehydrocyclization catalyst is described in U.S. Pat. No. 6,177,601, which is incorporated herein by reference. In this embodiment, the catalyst is a large pore molecular sieve catalyst as described above containing a uniformly distributed platinum-group metal component, and a tin component incorporated into the large pore molecular sieve by secondary synthesis. Suitable molecular sieves generally have a maximum free channel diameter or "pore size" of Å or larger, and preferably have a moderately large pore size of about 7 to 8 Å, and materials containing a significant amount of external surface. Such molecular sieves include those characterized as LTL, BPH, OFF, MOR, MTW, FAU, AFI, BEA, or MWW structure type by the IUPAC Commission on Zeolite Nomenclature, with the LTL structure being preferred. It is essential that the preferred L-zeolite be non-acidic, as acidity in the zeolite lowers the selectivity to aromatics of the finished catalyst. In order to be "non-acidic," the zeolite has substantially all of its cationic exchange sites occupied by nonhydrogen species. Preferably the cations occupying the exchangeable cation sites will comprise one or more of the alkali and alkaline earth metals, particularly Li, Na, K, Rb, Cs, Mg, Ca, Sr, and Ba. Other cationic species may be present alternatively or in addition to the foregoing. An especially preferred nonacidic L-zeolite is potassium-form L-zeolite.

The zeolites described above are typically combined with a binder in order to provide a convenient form for use in the catalyst particles of the present invention. The art teaches the suitability of a variety of refractory inorganic oxide binders. One or more of silica, alumina, or magnesia are preferred binder materials of the present invention. One or both of amorphous silica and alumina are especially preferred. In one embodiment, excellent results are obtained when using a synthetic white silica powder precipitated as ultra-fine spherical particles from a water solution. A silica binder preferably is nonacidic, contains less than 0.3 mass-% sulfate salts, and has a BET surface area of from about 120 to 160 $m^2/g$.

The xylene rich stream 190 is sent to an aromatics separation zone 195 where the aromatics stream 200 is separated from the alkylate stream 205.

The aromatics separation zone 195 generally comprises either solvent extraction, adsorptive separation, or a combination of solvent extraction and adsorptive separation in sequence to separate the products into a low-octane paraffin fraction and an aromatic-rich fraction. Solvent extraction separates essentially all of the paraffins and olefins, as well as the relatively smaller amounts of naphthenes, from an aromatic concentrate. Adsorptive separation selectively separates classes of paraffin and olefin isomers, depending on the adsorbent and operating conditions, with selected degrees of branching. Solvent extraction thus produces a concentrated aromatics stream, corresponding approximately to the aromatized product, and a concentrated aliphatic stream containing essentially all of the paraffins and olefins; in contrast, adsorptive separation generally produces a mixed aromatic-aliphatic stream and an aliphatic stream containing straight-chain and optionally lower-branched paraffins and olefins.

The aromatics stream 200 can then be recovered and sent for further processing to separate out the various aromatics.

In some embodiments, the alkylate stream 205 is mixed with the gasoline fraction 145 (or a portion thereof as described below).

In some embodiments, the gasoline fraction 145, which typically contains about 35-65 wt % aromatics, can be separated into an aromatic fraction 210 and a non-aromatic fraction 215. The aromatic fraction 210 can be sent to the aromatics extraction zone 195. In other embodiments, the whole gasoline fraction can be sent to the aromatics extraction zone 195.

The non-aromatic fraction 215 can be used for gasoline blending. In some embodiments, the alkylate stream 205 from the aromatics extraction zone 195 can be mixed with the non-aromatic fraction 215 of the gasoline fraction 145. The mixed stream can have a research octane number (RON) of 89-100, and a Reid vapor pressure (RVP) between 28 and 48 kPa (4 and 6.9 psi).

How much of the gasoline fraction 145 is sent for gasoline blending and how much is sent for aromatics extraction will depend on the needs and configuration of the refinery. When it is desired to increase the amount of aromatics produced, a larger proportion of the gasoline fraction 145 can be sent to the aromatics extraction zone 195. If the refiner wants more gasoline than aromatics while preserving high octane, lesser amounts of the gasoline fraction would be sent to the aromatics extraction zone 195. The proportion can range from 0 to 100%.

The light cycle oil fraction 150 can be recycled to the hydrotreating zone 110 and/or the FCC zone 120. It can be mixed with the $C_{9+}$ hydrocarbon stream 180 before being sent to the FCC zone 120, if desired. The ratio of light cycle oil to $C_{9+}$ hydrocarbons is generally in the range of about 1:1 to about 10:1 by volume. Higher ratios are preferred when the $C_{9+}$ hydrocarbon is rich in conjunct polymers or heavy hydrocarbons. In this case, the light cycle oil is a solvent solublizing the heavy materials.

Figure 2:
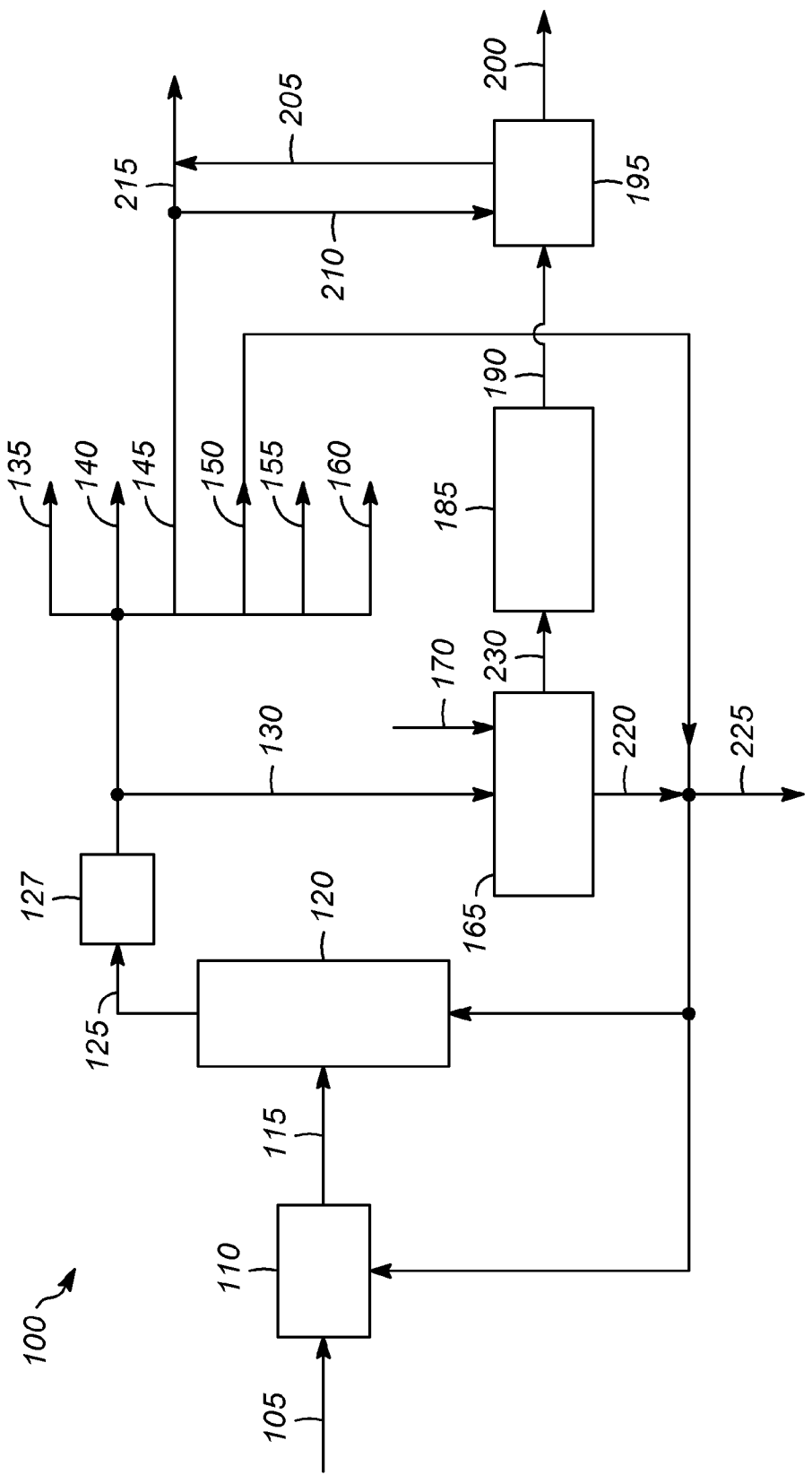
FIG. 2 is an illustration of another embodiment of a process for propylene and aromatics production using FCC and alkylation zones.

As shown in FIG. 2, the $C_4$-rich stream 130 is sent to an alkylation zone 165. The isobutane and 1-butene are selectively converted to dimethylhexanes (along with $C_{9+}$ hydrocarbons and $C_{7-}$ hydrocarbons) in the alkylation zone 165.

A portion 220 of the alkylation reaction product is mixed with at least a portion of the light cycle oil stream 150 to form a distillate product stream 225. The distillate product stream 225 has a high Cetane value because of the conjunct polymer in the alkylate reaction product.

The rest of the light cycle oil stream 150 can be recycled to the FCC zone 120 and/or the hydrotreating zone 110. The recycle portion of the light cycle oil stream will typically be in the range of about 10 vol % to about 75 vol % of the total light cycle oil stream 150.

The remainder of the alkylation reaction product 230 is sent to the dehydrocyclization zone 185 and processed as described above.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. An integrated fluid catalytic cracking (FCC) and alkylation process comprising:
    contacting a heavy hydrocarbon feedstock with an FCC catalyst in a fluidized reactor zone at effective conditions to produce an FCC effluent comprising light olefins and a range of hydrocarbons;
    separating the FCC effluent in a separation zone to obtain at least a $C_4$-rich hydrocarbons stream comprising isobutane and 1-butene, a gasoline stream comprising aromatics, and a propylene stream;
    contacting the $C_4$-rich hydrocarbons stream in an alkylation reaction zone with an alkylation catalyst under effective conditions to alkylate isobutane and 1-butene to produce a reaction product mixture comprising dimethylhexanes and $C_{9+}$ hydrocarbons;
    contacting at least a portion of the reaction product mixture in an aromatization zone with a dehydrocyclization catalyst under effective conditions to produce a dehydrocyclization effluent stream comprising xylenes;
    introducing the dehydrocyclization effluent stream and at least a first portion of the gasoline stream to an aromatics separation zone to obtain a xylenes-rich stream and an alkylate stream comprising isoheptane and isooctane;
    mixing the alkylate stream with at least a second portion of the gasoline stream; and
    recovering the propylene stream.

2. The process of claim 1 further comprising:
    separating the reaction product mixture into a stream rich in dimethylhexanes and a stream rich in C9+ hydrocarbons before the step of contacting at least a portion of the reaction product mixture in an aromatization zone; and
    wherein the step of contacting at least a portion of the reaction product mixture in an aromatization zone with a dehydrocyclization catalyst under effective conditions to produce a dehydrocyclization effluent stream comprising xylenes comprises contacting the stream rich in dimethylhexanes in an aromatization zone to form the dehydrocyclization effluent stream comprising xylenes.

3. The process of claim 2 further comprising recycling the stream rich in $C_{9+}$ hydrocarbons to the fluidized reactor zone.

4. The process of claim 2, further comprising:
    separating a light cycle oil stream from the FCC effluent stream;
    mixing at least a portion of the light cycle oil stream with the stream rich in C9+ hydrocarbons to form a mixed stream; and
    recycling the mixed stream to the fluidized reactor zone.

5. The process of claim 2 wherein the stream rich in dimethylhexane has a ratio of dimethylhexane to trimethylpentane of at least about 2:1.

6. The process of claim 2 further comprising:
    separating the gasoline stream into an aromatic fraction and a non-aromatic fraction;
    wherein the step of introducing at least the first portion of the gasoline stream into the aromatics separation zone comprises introducing the aromatic fraction into the aromatics separation zone; and
    wherein the step of mixing the alkylate stream from the aromatics separation zone with at least the second portion of the gasoline stream comprises mixing the alkylate stream from the aromatics separation zone with the non-aromatic fraction of the gasoline stream.

7. The process of claim 1 further comprising:
    hydrotreating the heavy hydrocarbon feedstock in a hydrotreating zone before contacting the heavy hydrocarbon feed with the FCC catalyst.

8. The process of claim 7, further comprising:
    separating a light cycle oil stream from the FCC effluent stream; and
    mixing at least a portion of the light cycle oil stream with the heavy hydrocarbon feedstock before hydrotreating the heavy hydrocarbon feedstock.

9. The process of claim 1 further comprising:
    introducing an isobutane-rich stream into the alkylation reaction zone.

10. The process of claim 9 wherein the isobutane-rich stream is produced by isomerizing a stream comprising n-butane.

11. The process of claim 1 wherein the alkylation catalyst comprises an ionic liquid catalyst.

12. The process of claim 1 wherein a ratio of isobutane to 1-butene in the alkylation zone is in a range of about 1:1 to about 50:1 by mole ratio.

13. The process of claim 1 wherein the $C_4$-rich hydrocarbons stream contains less than about 50 wt % total of 2-butene and isobutene.

14. The process of claim 1, further comprising:
    separating a light cycle oil stream from the FCC effluent stream;
    mixing at least a portion of the light cycle oil stream with a second portion of the reaction product mixture to form a mixed stream; and
    recovering the mixed stream.

15. An integrated fluid catalytic cracking (FCC) and alkylation process comprising:
    contacting a hydrotreated heavy hydrocarbon feedstock with an FCC catalyst in a fluidized reactor zone at effective conditions to produce an FCC effluent comprising light olefins and a range of hydrocarbons;
    separating the FCC effluent in a separation zone to obtain at least a $C_4$-rich hydrocarbons stream comprising isobutane and 1-butene, a light cycle oil stream, a gasoline stream comprising aromatics, and a propylene stream;
    contacting the $C_4$-rich hydrocarbons stream in an alkylation reaction zone with an alkylation catalyst under effective conditions to alkylate isobutane and 1-butene to produce a reaction product mixture comprising dimethylhexanes and $C_{9+}$ hydrocarbons;

separating the reaction product mixture into a dimethylhexanes-rich stream and a $C_{9+}$ hydrocarbons-rich stream;

contacting the dimethylhexanes-rich stream in an aromatization zone with a dehydrocyclization catalyst under an effective conditions to produce a dehydrocyclization effluent stream comprising xylenes;

introducing the dehydrocyclization effluent stream and at least a first portion of the gasoline stream to an aromatics separation zone to obtain a xylenes-rich stream and an alkylate stream comprising isoheptane and isooctane;

mixing the alkylate stream with at least a second portion of the gasoline stream;

mixing at least a portion of the light cycle oil stream with the $C_{9+}$ hydrocarbons-rich stream and recycling this mixed stream to the fluidized reactor zone; and recovering the propylene stream.

16. The process of claim 15, further comprising:

separating the gasoline stream into an aromatic fraction and a non-aromatic fraction;

wherein the step of introducing at least the first portion of the gasoline stream into the aromatics separation zone comprises introducing the aromatic fraction into the aromatics separation zone; and wherein the step of mixing the alkylate stream from the aromatics separation zone with at least the second portion of the gasoline stream comprises mixing the alkylate stream from the aromatics separation zone with the non-aromatic fraction of the gasoline stream.

* * * * *